(12) United States Patent
Schonhardt et al.

(10) Patent No.: US 9,301,789 B2
(45) Date of Patent: Apr. 5, 2016

(54) OSTEOSYNTHESIS PLATE FOR TREATMENT OF FRACTURES OR OSTEOTOMIES IN THE VICINITY OF JOINTS

(75) Inventors: Juergen Schonhardt, Rheinfelden (DE); Thomas Glanzmann, Morges (CH); Joanna Norstroem, Basel (CH); William B. Geissler, Brandon, MI (US)

(73) Assignee: Medartis AG, Basel (CH)

( * ) Notice: Subject to any disclaimer, the term of this patent is extended or adjusted under 35 U.S.C. 154(b) by 100 days.

(21) Appl. No.: 12/980,580

(22) Filed: Dec. 29, 2010

(65) Prior Publication Data

US 2011/0160730 A1    Jun. 30, 2011

(30) Foreign Application Priority Data

Dec. 30, 2009  (EP) .................................... 09180946

(51) Int. Cl.
*A61B 17/80*  (2006.01)
*A61B 17/08*  (2006.01)

(52) U.S. Cl.
CPC ........... *A61B 17/8061* (2013.01); *A61B 17/085* (2013.01)

(58) Field of Classification Search
CPC . A61B 17/80; A61B 17/8061; A61B 17/8085
USPC ...................... 606/280–299, 70, 71, 902–906
See application file for complete search history.

(56) References Cited

U.S. PATENT DOCUMENTS

| | | | |
|---|---|---|---|
| 6,506,191 B1 * | 1/2003 | Joos | 606/86 B |
| 6,960,211 B1 * | 11/2005 | Pfefferle et al. | 606/282 |
| 2004/0097936 A1 * | 5/2004 | Ebid | 606/69 |
| 2005/0065521 A1 * | 3/2005 | Steger et al. | 606/69 |
| 2005/0165401 A1 * | 7/2005 | Pack | 606/69 |
| 2007/0238069 A1 * | 10/2007 | Lovald et al. | 433/173 |
| 2007/0276386 A1 | 11/2007 | Gerlach et al. | |
| 2008/0051786 A1 * | 2/2008 | Jensen | 606/61 |
| 2008/0281327 A1 * | 11/2008 | Helfteren | 606/71 |
| 2009/0069851 A1 * | 3/2009 | Gillard et al. | 606/280 |
| 2009/0125069 A1 * | 5/2009 | Sixto, Jr. et al. | 606/286 |
| 2009/0318920 A1 * | 12/2009 | Jacobs | 606/70 |

FOREIGN PATENT DOCUMENTS

| | | |
|---|---|---|
| DE | 10125092 | 12/2001 |
| EP | 1464295 | 10/2004 |
| GB | 2451187 | 1/2009 |
| WO | 98/44849 | 10/1998 |
| WO | 03/007832 | 1/2003 |
| WO | 2006/031692 | 3/2006 |

* cited by examiner

*Primary Examiner* — Kevin T Truong
*Assistant Examiner* — Si Ming Ku
(74) *Attorney, Agent, or Firm* — Davis & Bujold PLLC; Michael J. Bujold

(57) ABSTRACT

An osteosynthesis plate according to the invention has at least two legs, which are spaced apart and interconnected by at least one bridge element. The legs each have a certain length and extend in the longitudinal direction from an epiphyseal to a diaphyseal end of the osteosynthesis plate. Moreover, each leg has at least one opening for holding an anchoring element. The size and shape of the bridge element and the legs are configured such that the legs may be applied on both sides of a bone in the region of a joint, preferably on the olecranon.

1 Claim, 7 Drawing Sheets

Figure 1:
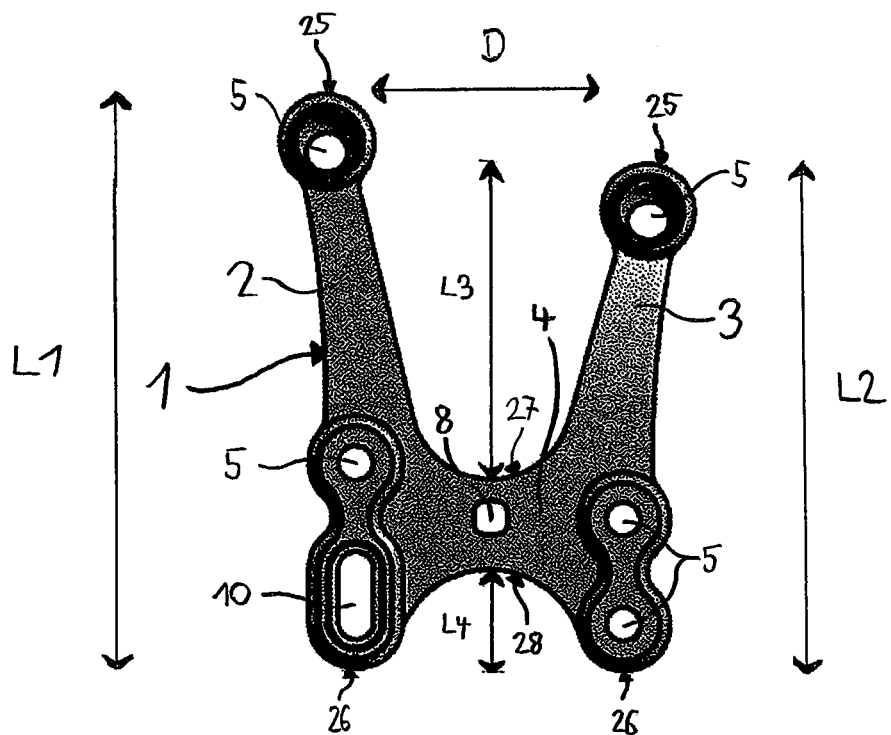

OSTEOSYNTHESIS PLATE FOR TREATMENT OF FRACTURES OR OSTEOTOMIES IN THE VICINITY OF JOINTS

The invention relates to an osteosynthesis plate according to the preamble of claim 1. The aim of such an osteosynthesis plate is to reliably attend to a fracture or osteotomy site on a bone, with a low risk of postsurgical complications.

Osteosynthesis plates for implanting, anatomical repositioning and internal splinting of bone fragments after fractures or osteotomies are widely known. By now, osteosynthesis plates have been developed for a wide variety of bones and fracture types.

Fractures and/or osteotomies that lie in the vicinity of a joint are a particular challenge in the development of novel osteosynthesis plates because the bone density is reduced and there is much soft tissue in the form of muscle tendons and ligaments radiating into the bone. Hence, an osteosynthesis plate should injure as little of this soft tissue as possible when inserted and there should be as little adverse effect as possible on the movement of the joint by the inserted osteosynthesis plate. However, the osteosynthesis plate should still be stable enough to absorb tensile and torsional forces acting on the bone in this region.

In the following text, the problem will be explained in an exemplary fashion with the aid of the olecranon.

The olecranon is the proximal end of the ulna. It is thickened and merges into a wide bone spur (tuber olecrani), which is elongated like a beak. The upper surface of the bone spur is approximately rhombic and roughened where the triceps tendon (musculus triceps brachii) radiates into the bone. The goal of treating fractures or osteotomies in the vicinity of the olecranon is the reconstruction of the joint area and restitution of the integrity of the musculoskeletal system. This requires special fixations.

Non-dislocated and non-comminuted transverse fractures of the olecranon are relatively simple to treat by immobilization using an upper arm splint. However, the most common type of fracture of the olecranon are dislocated, non-comminuted fractures. Tension band wiring is the established treatment technique for such fractures. In the process, the two bone fragments firstly are set and two parallel Kirschner wires are inserted obliquely from proximal to distal. Then a hole is drilled transversely through the distal fragment. A cerclage wire is then guided around the Kirschner wires and through the distal transverse hole on the dorsal side of the ulna in a figure of eight. The formation of wire loops on the sides affords the possibility of compressing the fracture by twisting these loops. In the process, the cerclage wire converts tensile forces from the triceps into pressure forces in the fracture gap.

Complications frequently occur when tension band wiring is used. The most common complication is a painful subcutaneous prominence of the wires, often as a result of proximal migration of the Kirschner wires. There can also be problems due to the sharp-edged wire ends of the cerclage wire, which can lead to injury or irritation of the soft tissue. As a result of the high tensile forces occurring on the cerclage wire, there may additionally be damage to the bone or the wire may be pulled out in the region where the wire leaves the bore. Moreover, tension band wiring does not always offer sufficient stability to ensure the long-term correct reconstruction of the bone. Moreover, the bone may break out when the transverse bore is set.

The surgical procedure for setting a cerclage wire is sometimes demanding because various parameters have to be monitored at the same time. Thus, it should be ensured that the Kirschner wires remain parallel and the cerclage wire should not cross over the fracture or osteotomy line. Moreover, generating an even compression force by twisting the cerclage wire is awkward and it is difficult to correct an uneven compression.

U.S. Pat. No. 7,037,308 describes an implant substantially based on the tension band principle. The described implant consists of two legs arranged in parallel that can be inserted into the bone from proximal to distal and over the fracture site, which legs are connected by means of a wire-like section of the implant resting against the bone surface. The section resting against the bone surface starts off at one of the legs and extends over the fracture site from the proximal to the distal side, describes an arc on the distal fragment and then returns from the distal to the proximal side and to the second leg. One embodiment provides for the two parts that lead from the proximal to the distal side and from the distal to the proximal side to cross once in front of the arc. The implant is fixed on the distal fragment by means of a screw. Accordingly, the implant unifies all elements of the tension band in a single part.

A disadvantage of this implant is that the section resting against the bone is situated on the dorsal side of the ulna, and this restricts the patient after surgery by virtue of the fact that the elbow and forearm cannot be rested on something without pain. Moreover, a further disadvantage lies in the fact that the tensile forces are absorbed by only a few—in most cases only one—bone screws. This leads to a high load on the bone in the vicinity of the screws. Furthermore, the position of the implant on the medial side of the bone can lead to irritation of the surrounding soft tissue. As a result of this positioning, the implant can also be felt through the skin, which can lead to uneasiness in some patients. Moreover, a target instrument appears to be necessary for setting this implant.

In the case of comminuted, dislocated and stable fractures of the olecranon, the most common treatment method in patients under the age of 60 are anatomical repositions of the bone fragments and subsequent fixations using an osteosynthesis plate.

Unstable fractures are preferably likewise treated by plate fixation. In the case of this type of fracture, the utilized osteosynthesis plate must have increased stability in addition to absorbing tensile forces because it must bridge a plurality of fragments, which, moreover, are lacking or have an impaired interfragmentary support.

U.S. Pat. No. 3,716,050 describes such an osteosynthesis plate. The osteosynthesis plate is embodied in an "L" shape and is fixed to the dorsal edge of the ulna, with the shorter arm of the "L" resting on the proximal surface of the olecranon.

A whole host of olecranon osteosynthesis plates are commercially available, for example the "LCP Olecranon" by Synthes Inc., or the "Peri-LOC Olecranon locking plate" by Smith & Nephew. These osteosynthesis plates all rest on the dorsal side of the ulna, and have bent projections that come to rest on the proximal surface of the olecranon.

A disadvantage of these osteosynthesis plates is that the bent projections engage in the region where the triceps tendon radiates in. Thus, this tendon is partially severed or at least forced into a non-physiological position when the osteosynthesis plate is inserted. A further disadvantage of these osteosynthesis plates lies in their position on the dorsal edge of the ulna. This impedes the patient after surgery because the elbow and the forearm cannot be rested on something without pain. The skin situated above the implant is exposed such that skin necroses are not exceptional at this position. Moreover, depending on the thickness of the osteosynthesis plate, the contours thereof may be visible through the skin, which can lead to uneasiness in some patients. Moreover, the plate may restrict the mobility of the joint depending on the length of the projection. The aforementioned disadvantages make it highly likely that the implants have to be removed again after some time, which is connected with additional costs and again puts stress on the patient as a result of the second intervention.

Hence, the object of the invention consists of developing an implant of the type mentioned at the outset, which prevents the disadvantages of the known prior art and thus allows stable care of a fracture or osteotomy in the vicinity of the joint with the lowest possible risk of postsurgical complications. According to the invention, this object is achieved by an osteosynthesis plate with the features of claim 1.

The osteosynthesis plate according to the invention comprises at least two legs, which are spaced apart and interconnected by at least one bridge element. The legs each have a certain length and extend in the longitudinal direction from an epiphyseal to a diaphyseal end of the osteosynthesis plate. Moreover, both legs each comprise at least one opening for holding an anchoring means. The size and shape of the at least one bridge element and the at least two legs are embodied such that the legs can be applied to a bone on both sides, more particularly in the region of a joint, preferably on the olecranon.

Within the scope of this application, legs are understood to be parts of an osteosynthesis plate which are designed such that they can be placed over a fracture or osteotomy site. The bridge element is understood to encompass those parts of an osteosynthesis plate which interconnect the legs and keep them at a defined distance from one another.

The design of the plate with at least two lateral legs and at least one bridge element allows stable support of a fracture or osteotomy site in a bone region close to the joint, without the area of the bone where tendons and/or ligaments radiate in being covered by the plate. Moreover, areas that are only covered by a small amount of soft tissue, but are used in everyday life as supports, are spared by the plate. Here, the at least one bridge element is positioned such that it does not cover this region. In the case of the olecranon, in particular, the risk of skin necroses or soft-tissue inflammations in the region of the dorsal edge of the ulna is substantially reduced because the thin skin in this region is not additionally strained by a plate lying thereunder.

The size is understood to mean the external dimensions of the legs such as width, length and thickness, but also the profile thereof.

The legs are particularly preferably configured such that they can be bent far enough in all planes so that they can be fitted to the bone anatomy in an optimum fashion. Thus, on osteosynthesis plate with defined dimensions may be fitted to the individual anatomical peculiarities of a patient. In particular, this allows the legs to be fitted such that the regions where ligaments and/or tendons radiate into the bone are not impaired.

In a further embodiment of the osteosynthesis plate according to the invention, the at least one bridge element and the at least two legs are designed such that the at least one bridge element can be placed or adapted over the dorsal edge of the bone from the lateral to the medial side and the at least two legs can be fitted to the lateral anatomical conditions of the bone. As a result, the areas of the bone where tendons and ligaments radiate in are not covered by the plate. Accordingly, the ligaments and tendons are barely injured or impaired by the plate. Moreover, a further substantial advantage lies in the fact that the configuration of the osteosynthesis plate with lateral legs and the relatively thin bridge element on the dorsal edge does not put additional strain on the soft tissue, in particular the skin, when the patient uses these for support. There may be postsurgical pains or complications when the patient uses these for support in the case of a purely dorsal fixation.

Within the scope of the invention, the epiphyseal end is understood to be the end of the osteosynthesis plate which points in the direction of the epiphysis of the bone, i.e. the end closer to the joint, when used as intended. Accordingly, the diaphyseal end of the osteosynthesis plate lies in the direction of the diaphysis of the bone and thus further away from the joint.

The osteosynthesis plate is used for attending to fractures or osteotomies of the bone. According to a first indication, the osteosynthesis plate is used for attending to simple fractures or osteotomies situated in the vicinity of a joint. The bones are bones from the human musculoskeletal system. The osteosynthesis plate is particularly preferably designed such that it can be fitted to treat fractures or osteotomies in regions in the vicinity of a joint of a tubular bone, for example the distal tibia, the proximal radius, the proximal ulna or the distal humerus. The osteosynthesis plate according to the invention is particularly preferably used for treatment of fractures or osteotomies of the olecranon. Osteotomies in the region of the olecranon are typically carried out to create an access by folding back the triceps in the case of fractures of the distal humerus. According to the prior art, such simple fractures and osteotomies are typically attended to by so-called tension bands. In the case of such a treatment, the application of forces in the longitudinal direction is particularly relevant. In such indications, special torsional stiffness of the osteosynthesis plate is less relevant.

According to another indication of the osteosynthesis plate according to the invention, the osteosynthesis plate is used to treat comminuted or dislocated fractures. Alternatively, an osteosynthesis plate according to the invention can also be utilized for fractures where regions of the bone cannot be reconstructed and there are so-called "defect zones". In these cases, the osteosynthesis plate according to the invention has a more stable design such that it can also absorb further forces.

It is particularly preferable for the legs to be designed such that they can be fitted over the external curvature of the epiphysis by bending, i.e. they can be guided in part around the epiphysis of the bone. More particularly, this allows an anchoring element to be inserted into the bone in approximately the distal direction through an opening in the vicinity of the epiphysis. This allows further interfragmentary compression.

The at least two legs and the at least one bridge element are preferably arranged such that a region on one side of the fracture line is not covered by the plate. From the edge of the epiphysis, this region should extend at least 20 mm, preferably at least 30 mm, in the direction of the bone diaphysis. Such a configuration is advantageous since the region of the bone in the vicinity of the joint where ligaments and tendons radiate into the bone is not covered by the plate.

The legs of the osteosynthesis plate may be provided in a state that has been bent in advance and/or that a surgeon may bend manually and/or by using bending tools during the operation.

The legs are preferably provided in the form of elongate plates, particularly for applications for treating fractures. The edges and corners of these plates are preferably rounded off. One embodiment of the invention provides for the legs to have a wave-like design in the plane of the plate. A further embodiment additionally provides for the legs to be tapered between the regions with the openings. An alternative embodiment additionally provides for the legs to be available in the form of a wire or a plurality of wires situated next to one another between the regions with the openings. Furthermore, the legs can be embodied in the form of a band or a plurality of bands situated next to one another.

The distance between the legs can vary depending on the indication for which the osteosynthesis plate is provided. However, it should always be of such a size that the two legs can be placed laterally against the bone. A particular embodiment provides for the distance between the legs to increase and/or decrease over the length of the osteosynthesis plate. As a result, the plate can, depending on the intended indication, be adapted such that the legs can be placed laterally against the bone over their entire length.

The two legs may also be provided with a curvature of a certain radius. A further embodiment of the invention additionally provides for the legs to have a wave-like design in the plane of the plate, with the distance between the legs changing periodically over the length of the osteosynthesis plate. In a particularly preferred embodiment, the distance between the legs increases in the longitudinal direction towards the epiphyseal end. As a result of this arrangement, the at least two legs avoid the zones of the nearby joint where the tendons and ligaments radiate into the bone and may also be easily fitted to the lateral anatomy of the bone.

The legs each comprise at least two openings for holding anchoring elements. The legs are thicker in the region of the openings, i.e. within a certain radius around the openings, than in the regions between the openings in applications relating to osteotomies or simple fractures. Another embodiment, in particular for treating complicated fractures, provides for the legs to have the same thickness over their entire surface. The diameter of the openings is selected such that sufficiently strong anchoring elements may be utilized, depending on the intended indication.

By way of example, bone screws, pins, wires or the like are suitable anchoring elements.

In the case of an osteosynthesis plate which may be fitted for treating a fracture or an osteotomy of the olecranon, the diameter of the openings is between 1.5 mm and 3.5 mm, preferably between 2.5 mm and 3.0 mm.

The bridge element is preferably embodied such that it is less thick than the legs in the region of the openings; preferably said bridge element is half as thick. It is particularly preferable for the bridge element to be less thick than the smallest thickness of the legs. If the osteosynthesis plate according to the invention is designed such that it can be used to treat a bone defect on the olecranon, a bridge element that is as thin as possible has the substantial advantage that the patient is barely impaired by the osteosynthesis plate after surgery when resting the elbow or the forearm. Moreover, this prevents the contours of the osteosynthesis plate from becoming visible through the skin. The bridge element should have a thickness of between 0.1 mm and 0.7 mm, preferably of between 0.2 mm and 0.6 mm in the case of such an osteosynthesis plate. As a result of this arrangement, the at least one bridge element can be bent in its entirety over the dorsal edge of the ulna. This affords the possibility of placing the legs on both sides of the ulna without the latter coming to rest too close to the dorsal edge.

Preferably the bridge element is configured as a plate or band. In another embodiment for the application in e.g. osteotomies, the bridge element may however also be embodied in the form of a wire. However, the bridge element should be configured such that it may be fitted intraoperatively to the curvature of the bone surface. The at least one bridge element may preferably be bent manually without it buckling.

The osteosynthesis plate according to the invention may also comprise more than one bridge element; however, the osteosynthesis plate preferably has 1, 2 or 3 bridge elements. The bridge elements are preferably, always configured such that, towards a first end of the plate, more particularly the epiphyseal end, a bridge element does not connect the shorter leg to the longer leg over at least 15 mm of the length of said shorter leg. Alternatively, the bridge elements are configured such that, towards a first end of the plate, more particularly the epiphyseal end, the shorter leg is not connected to the longer leg over at least 60% of the length of said shorter leg. If both legs have the same length, the at least one bridge element is configured such that the legs are not interconnected over at least 15 mm or alternatively at least 60% of their length in the longitudinal direction, preferably towards a first end of the plate, more particularly the epiphyseal end. As a result, the plate can be pushed over the fracture from one side, either from the epiphyseal or the diaphyseal side, without pushing the at least one bridge element over the region in which the tendons and/or ligaments radiate into the bone.

The shorter leg, which preferably is not connected to the second or longer leg towards a first end of the plate, is at least 15 mm, preferably at least 18 mm, more preferably at least 20 mm long in the case of an osteosynthesis plate for treating a fracture or an osteotomy of the olecranon. This prevents the bridge element from coming to lie in the region where the triceps radiates into the ulna. The length of the legs is nevertheless sufficient for applying these up to the proximal/epiphyseal end of the olecranon.

The at least one bridge element preferably comprises at least one opening, which is preferably arranged centrally on the bridge element. Compared to a bridge element without an opening, this at least one opening allows higher stiffness with respect to torsional loads in the case of the same cross-sectional area, without impairing the ability to bend. Moreover, this reduces the resting surface of the implant on the periosteum, which is advantageous for the arterialvenous circulation. The bridge element is most preferably designed as a mesh structure, i.e. it consists of many partly intercrossing bridge elements. Such a structure makes it easier to adapt the bridge element to the variability of the bones.

The legs may have any cross-sectional shape. The legs preferably have a rectangular cross section, with the edges being rounded off to avoid damaging or irritating the soft tissue. Circular, semicircular, trapezoidal or generally polygonal cross sections are further preferred cross sections.

The two legs preferably have different lengths, but may also have the same length. The length of the legs is primarily dependent on the bone for which the osteosynthesis plate is provided. Depending on the indication of the plate, a longer leg is advantageously better suited to distribute occurring forces over the length of the bone or to be used for fixing further fragments.

The legs preferably have the same thickness over their entire length. In one preferred embodiment, the thickness can decrease in the direction of either the diaphyseal and/or the epiphyseal end of the osteosynthesis plate. The legs may have the greatest thickness in the vicinity of the bridge element. The legs are more preferably thicker in the vicinity of the openings than in the regions between the openings. The thickness of the legs can be reduced compared to the region of the openings, particularly for indications such as osteotomies or fractures with intrafragmentary support. The occurrences of soft-tissue inflammations or even necroses are minimized by the reduced thickness because less tissue is displaced compared to thicker plates.

In the case of an osteosynthesis plate provided for treatment of a fracture or an osteotomy of the olecranon, a first, longer leg has a length of between 30 mm and 200 mm, preferably between 40 mm and 60 mm, and the second, shorter leg has a length of between 30 mm and 50 mm, preferably between 30 mm and 40 mm. In this case, the distance between the legs is between 10 mm and 40 mm, preferably between 10 mm and 25 mm. At least in the region of the openings, the legs have a thickness of between 1.0 mm and 4.0 mm, preferably between 1.5 mm and 2.5 mm.

In an alternative embodiment of the invention, the at least one bridge element is arranged such that the legs are not interconnected in the direction of the second end of the plate, more particularly the diaphyseal end, over at least 2.5 mm or alternatively over at least 10% of the length of the shorter leg.

In the case of an osteosynthesis plate, which can be adapted for treating a fracture or an osteotomy of the olecranon, the distance between the bridge element and the diaphyseal end of the shorter leg is at least 3 mm, preferably at least 7 mm, more preferably at least 10 mm.

A further embodiment of the invention comprise two crossing bridge elements which interconnect the two legs and whose crossing region is arranged such that the distance between said region and the one end of the osteosynthesis plate, more preferably the epiphyseal end, is at least 15 mm of the length of the shorter leg. Alternatively, this distance is at least 60% of the length of the shorter leg.

The bridge elements have a shape that is substantially similar to the letter "X". The two bridge elements more preferably have a slight curvature. The transmission of any compression force produces only low stress peaks in the case of curved and crossing-over bridge elements.

At least one of the openings of the legs is preferably adapted to lock an anchoring element, particularly a screw. Locking technologies are known in the field of osteosynthesis. As a result, an osteosynthesis plate according to the invention may be anchored on a bone at a fixed angle. An anchoring element anchored at a fixed angle may loosen less after surgery, e.g. during physiotherapeutic aftercare, thus leading to less soft-tissue irritation.

Alternatively, the openings in the two legs may be arranged asymmetrically with respect to one another. This minimizes the probability of anchoring elements clashing together within the bone interior. Moreover, this likewise minimizes the probability of bone splitting or splintering. At least one opening is preferably configured such that an anchoring element may be inserted at an angle that differs from 90° with respect to the plane of the plate. The opening is preferably configured such that insertion at an angle in the range between 80° and 45° with respect to the plane of the plate is possible. Here the axis of the opening itself may be at an angle with respect to the plate. An alternative embodiment provides for the plate to be raised in the vicinity of such an opening in order to prevent a part of the bone anchor which was inserted at an angle from protruding. Such a raised opening is described in EP1861031. Insertion of an anchoring element at an angle that differs from 90° with respect to the plate surface allows for an anchoring which is optimally adapted to the anatomy and density of the bone.

Alternatively, at least one opening may be designed as a long-hole. This allows the osteosynthesis plate to be displaced if a compression force is applied onto the fracture or osteotomy site, thus reducing the risk of dislocating the proximal fragments. The long-hole is more preferably configured as a compression hole. Such a configuration of the long-hole results in the generation of a compression force acting on the fracture or osteotomy site when a bone screw is screwed in.

Each leg preferably comprises at least one opening at both the epiphyseal and at the diaphyseal end, respectively. This allows to fix the osteosynthesis plate on the bone secured against rotation and displacement. There may also be further openings between said openings.

In a particularly preferred embodiment of the invention, the osteosynthesis plate is configured such that at least one opening comes to rest on the epiphyseal bone fragment. Another, more preferred embodiment of the invention provides for each leg to have a plurality of openings, most preferably 2, 3, 4, 5, 6 or more openings. By way of example, this allows for a good treatment of comminuted fractures because as many fragments as possible may be fixed using as few anchoring elements as possible.

The osteosynthesis plate is preferably made of a biocompatible material, more preferably a biocompatible metal or a biocompatible alloy. By way of example, the osteosynthesis plate comprises titanium, stainless steel, a titanium alloy such as TAV (Ti6Al4V) or TAN (Ti6Al7Nb), a zirconium alloy or a magnesium alloy. Alternatively, the osteosynthesis plate may also made of a biocompatible, preferably degradable, polymer material.

A further aspect of the invention relates to a method for treating a fracture or an osteotomy of a bone, more particularly the olecranon, in the region of a joint. An osteosynthesis plate as described above is provided in a first step. This is followed by firstly adapting the at least one bridge element to the curvature of the bone in the region of a joint, more particularly the dorsal edge of the ulna, by bending. The legs are likewise adapted to the lateral anatomy of the bone by bending. The plate is more particularly attached to the bone using bone screws such that the two legs rest laterally against the bone. In the process, the region in the bones where the tendons and/or ligaments radiate into the bone preferably remain uncovered by the plate.

The epiphyseal ends of the legs of the osteosynthesis plate may preferably be guided around the proximal olecranon and may likewise be fixed in this region using anchoring elements.

Figure 2:
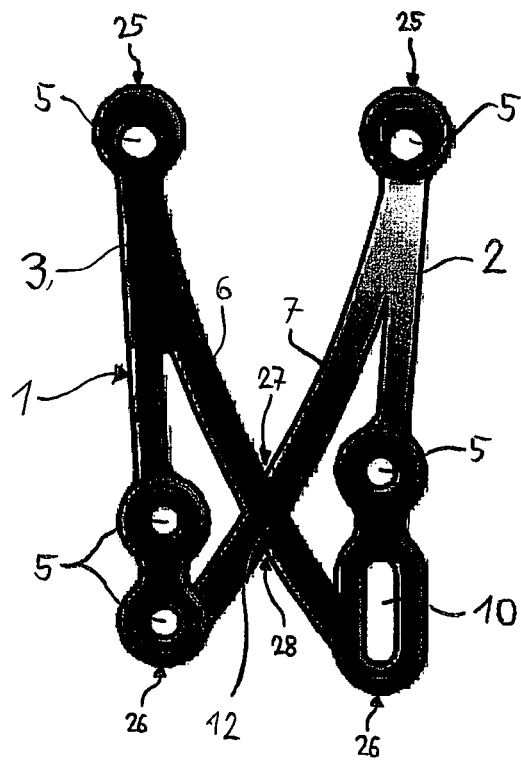
Figure 3:
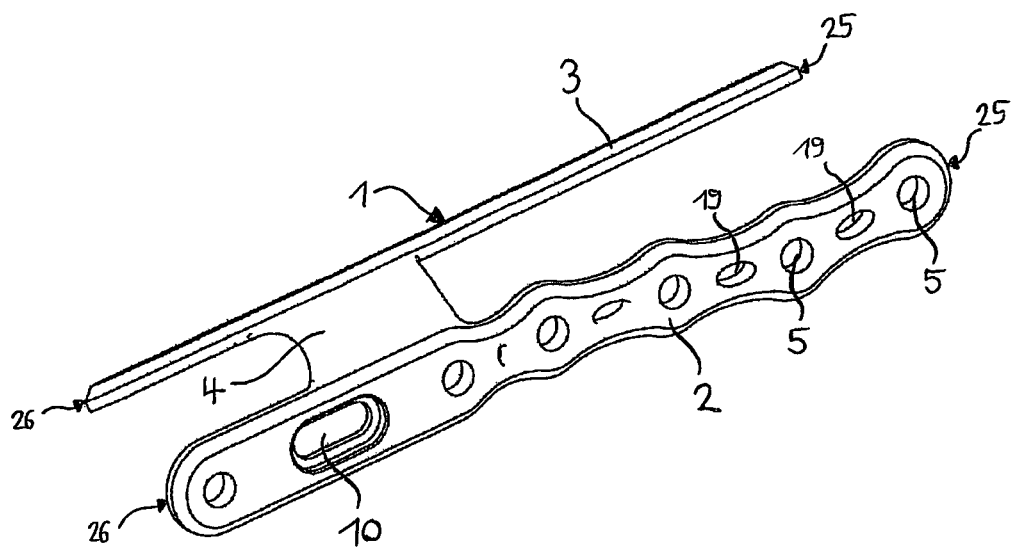
Figure 4:
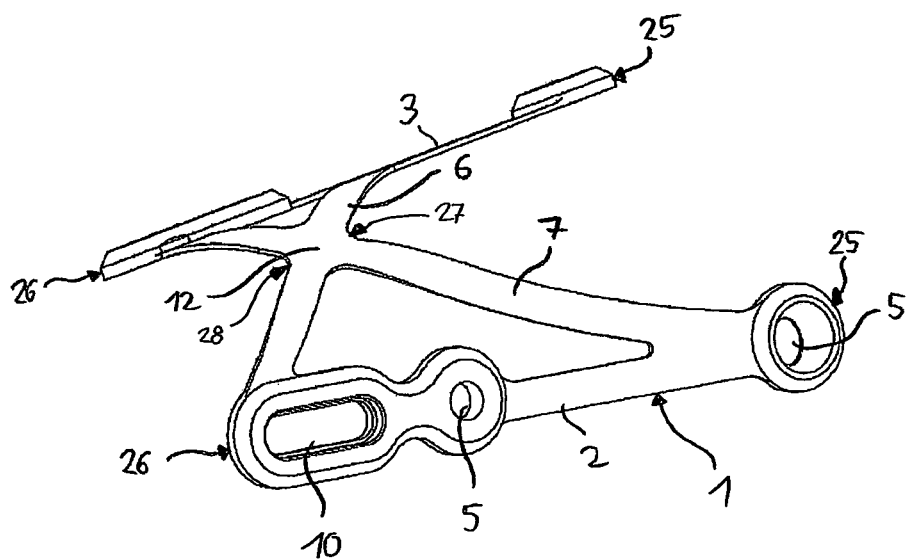
Figure 5:
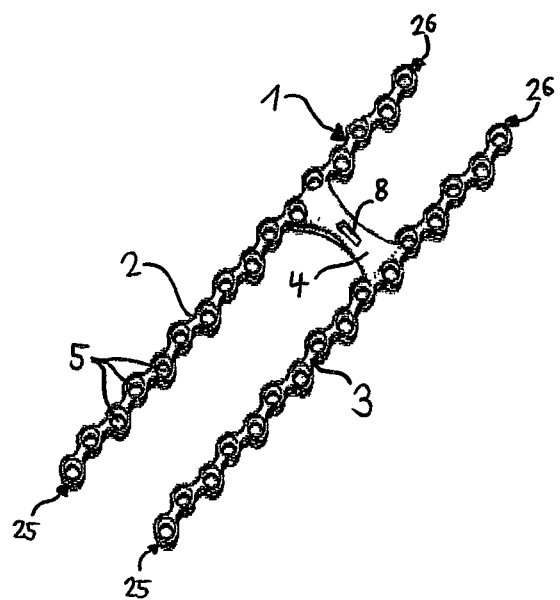
Figure 6:
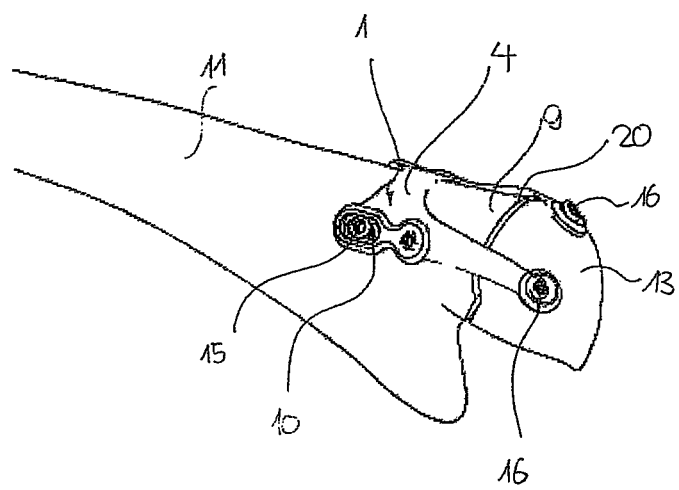
Figure 7A:
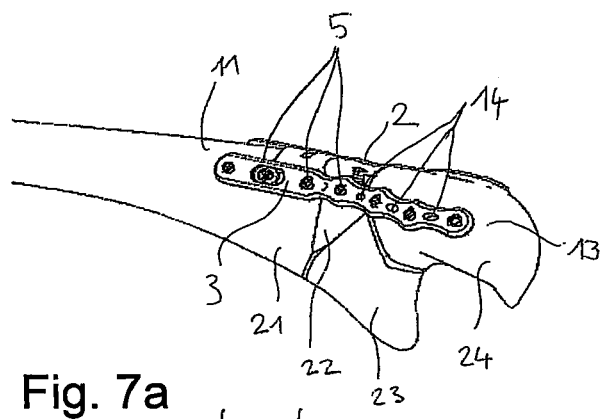
Figures 7B, 7C:
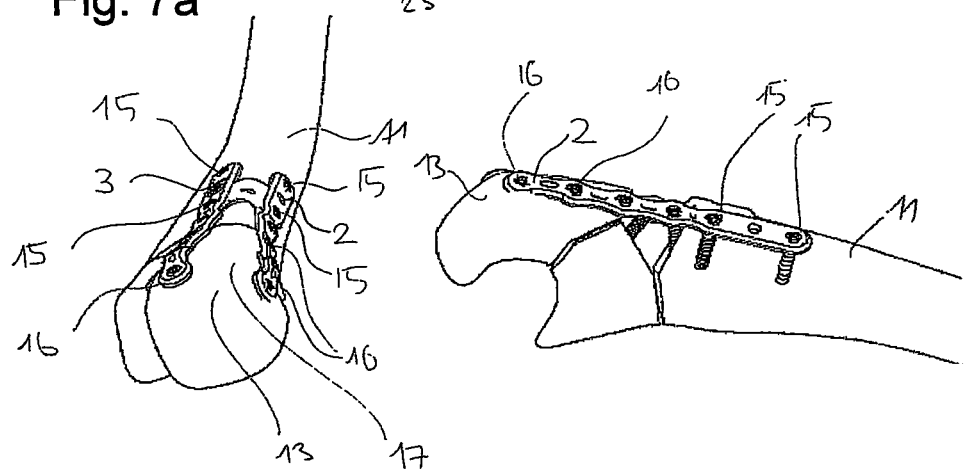
Figure 8:
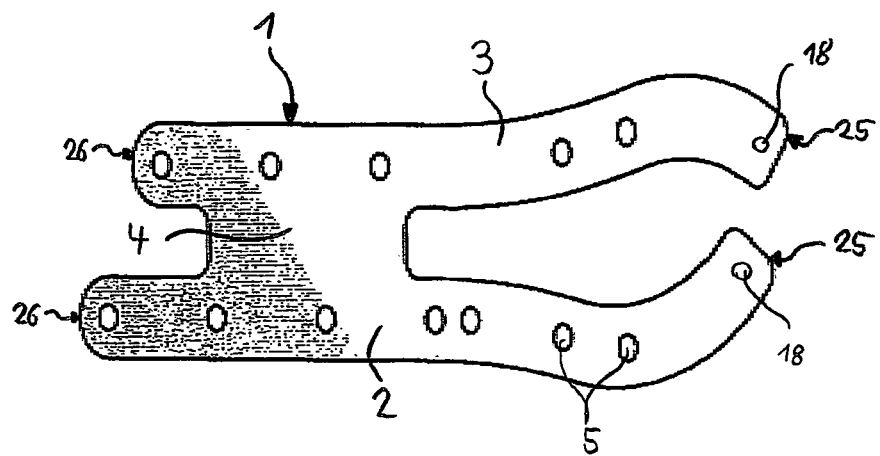
Figure 9:
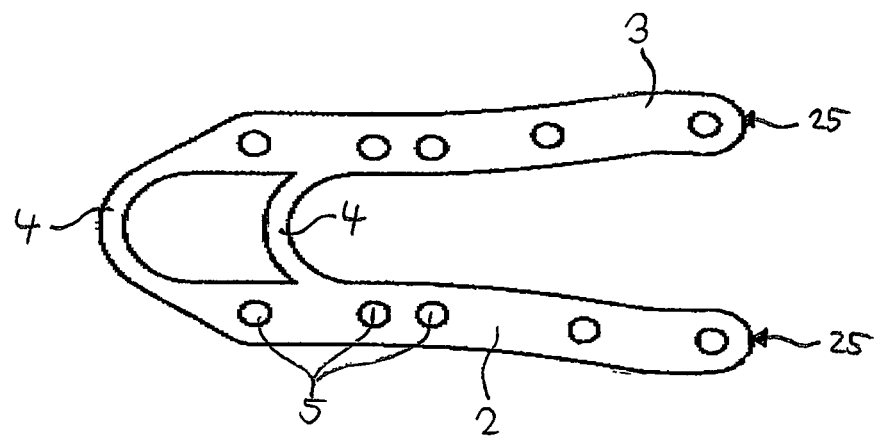
Figure 10:
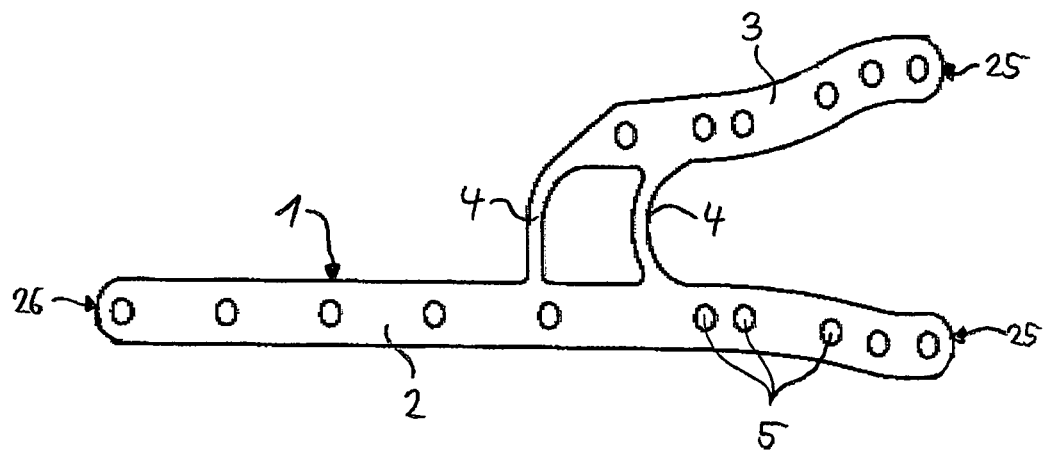
Figure 11:
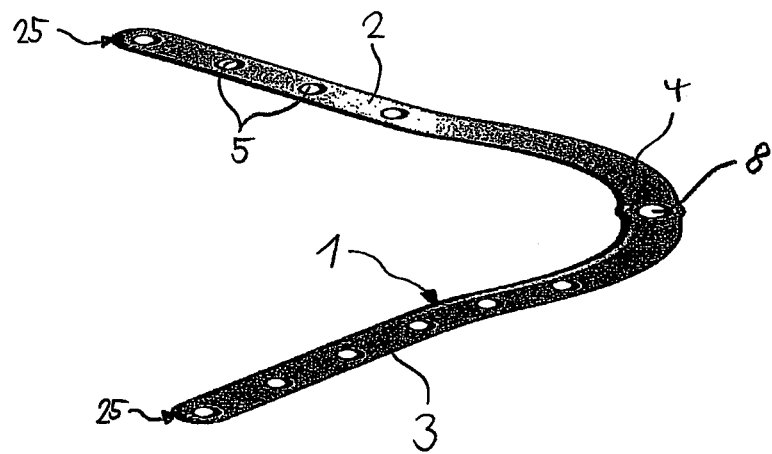
Figure 12:
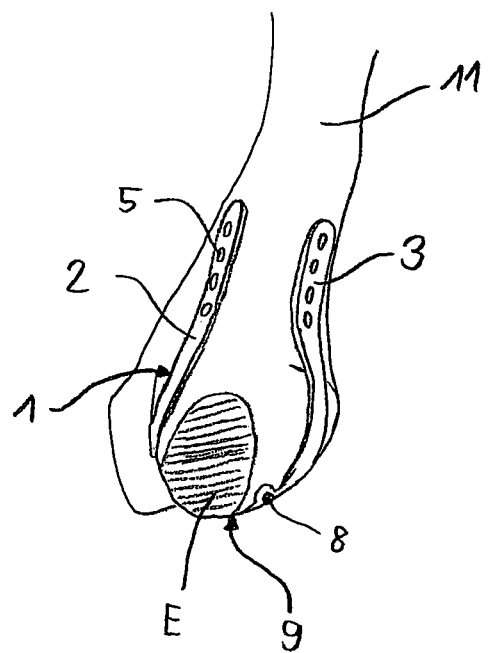
Figure 13:
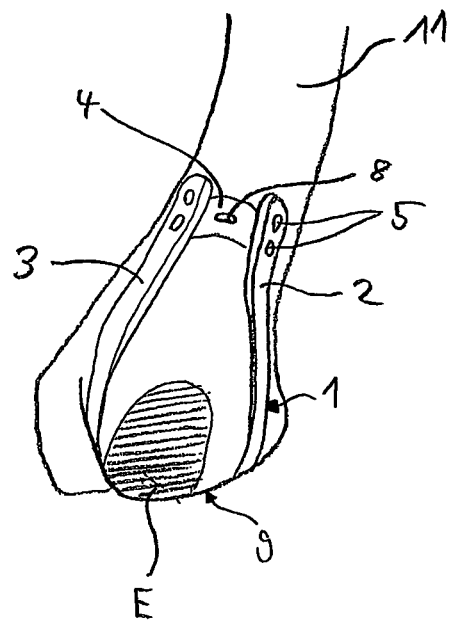

Further advantages and individual features of the invention will become apparent from the following exemplary embodiments and the figures, in which:

FIG. 1 shows a first embodiment of the osteosynthesis plate according to the invention with one bridge element, FIG. 2 shows a second embodiment of the osteosynthesis plate according to the invention with two crossing bridge element, FIG. 3 shows a further embodiment of the osteosynthesis plate according to the invention having a bridge element that has been bent in advance and notches in the legs, FIG. 4 shows the osteosynthesis plate from FIG. 2 in a state in which it has been bent in advance, FIG. 5 shows yet a further embodiment of the osteosynthesis plate according to the invention with snaking legs, FIG. 6 shows a perspective illustration of the osteosynthesis plate as per FIG. 1 for treatment of an osteotomy of the olecranon, FIGS. 7a to 7c show perspective illustrations of a further embodiment of an osteosynthesis plate for treating a comminuted fracture with a defect zone on the olecranon, FIG. 8 shows a further embodiment of the osteosynthesis plate with legs that have been bent in advance, FIG. 9 shows an osteosynthesis plate according to the invention with two bridge elements, FIG. 10 shows an alternative embodiment of the osteosynthesis plate shown in FIG. 9, FIG. 11 shows a further preferred embodiment of the osteosynthesis plate, in which the two legs are connected via their epiphyseal ends by a bridge element, FIG. 12 shows an exemplary application of a plate according to FIG. 11, FIG. 13 shows an exemplary application of an osteosynthesis plate with legs applied over the external curvature of the epiphysis.

FIG. 1 shows a first embodiment of the osteosynthesis plate 1 according to the invention. In the figure, the epiphyseal end 25 of the plate is illustrated at the top and the diaphyseal end 26 is illustrated at the bottom. A longer leg 2 has a length L1 and a shorter leg 3 has a length L2. The two legs 2, 3 are interconnected by a bridge element 4. Here, the bridge element 4 is embodied in the shape of a plate, with the epiphyseal edge 27 and the diaphyseal edge 28 of the bridge element 4 having a slight concave curvature. In this embodiment, the bridge element 4 has a centrally arranged notch 8. The two legs 2, 3 do not have a straight design but have a slight outward curvature in the longitudinal direction from the diaphyseal end 26 to the epiphyseal end 25. As a result, the distance D between the legs accordingly increases from the diaphyseal to the epiphyseal side. Respectively, one opening 5 is arranged at the epiphyseal end 25 of the legs 2, 3. The legs 2, 3 each have two openings 5 at the diaphyseal end 26, with one opening 5 in the longer leg 2 being embodied as a long-hole 10 in this embodiment. The thickness of the plate is slightly raised in the regions of the openings 5 and thus it is greater than in the regions between the openings 5.

In the case of the osteosynthesis plate 1 shown in FIG. 1, the longer leg 2 typically has a length L1 of 43 mm and the shorter leg 3 typically has a length L2 of 38 mm. In the vicinity of the bridge element 4, the plate, including the legs, has a width of 27 mm.

In the region of the legs 2, 3 away from the vicinity of the openings 5 and in the region of the bridge element 4, the osteosynthesis plate 1 has a thickness of 0.5 mm. In the vicinity of the openings 5, the plate thickness is 1.6 mm.

Thus, the legs 2, 3 are designed to be relatively thin in the exemplary embodiment shown in FIG. 1. However, as a result of their stability, the legs 2, 3 easily suffice to attend to a fracture or an osteotomy of a bone in the vicinity of the joint, in particular of the olecranon, because they only have to transfer tensile forces.

Moreover, according to an alternative embodiment (not illustrated), it is also feasible for the legs 2, 3 to be embodied like wires with a round cross section.

The bridge element 4 is clearly arranged adjacent to the diaphyseal end of the osteosynthesis plate 1. By way of example, the distance L3 between the epiphyseal end 25 of the shorter leg 3 and the epiphyseal edge 27 of the bridge element 4 can typically be approximately 24 mm, i.e. approximately 63% of the length L2 of the shorter leg 3. By contrast, the distance L4 between the diaphyseal end 26 of the shorter leg 3 of the osteosynthesis plate 1 and the diaphyseal edge 28 of the bridge element 4 is typically only approximately 7 mm.

FIG. 2 shows an alternative embodiment of an osteosynthesis plate 1 according to the invention. The plate 1 has been provided with two crossing bridge elements 6, 7. The two bridge elements 6, 7 are both slightly curved over a radius. In this embodiment, the crossing region 12 is arranged such that the epiphyseal edge 27, created as a result of the two bridge elements 6, 7 meeting, has a distance from the epiphyseal end 25 of the plate that is approximately 60% of the length of the shorter leg 3. Number and arrangement of the openings 5 and the long-hole 10 in this embodiment correspond to those in the embodiment in FIG. 1.

FIG. 3 shows a further alternative embodiment of an osteosynthesis plate 1 according to the invention. Here, the bridge element 4 of the osteosynthesis plate 1 has already been bent in advance. The two legs 2, 3 do not have a straight configuration, but are already slightly adapted to the contours of the lateral bone. The width of the legs 2, 3 is slightly smaller in the region between the openings 5 than in the vicinity of the openings 5. In these intermediate regions this embodiment of the osteosynthesis plate 1 has notches 19 that facilitate bending. One of the openings 5 is again designed as a long-hole 10.

FIG. 4 shows the osteosynthesis plate 1 from FIG. 2 in a state in which it has been bent in advance. The two crossing bridge elements 6, 7 are bent according to the contour of the bone. This figure clearly illustrates that the legs 2, 3 in the region between the openings 5, and the bridge elements 6, 7 are thinner than the legs 2, 3 in the vicinity of the openings 5. Since it is mainly tensile forces that have to be transmitted in the case of simple fractures, the legs 2, 3 may have a correspondingly thin design.

FIG. 5 shows a further alternative embodiment of the osteosynthesis plate 1 according to the invention. The legs 2, 3 are designed such that the openings 5 do not lie on a straight line but are respectively offset in the lateral direction with respect to one another. The shape of the legs 2, 3 is similar to a snaking line. The legs 2, 3 are less wide between the openings 5 than in the vicinity of the openings 5. This makes it easier to fit the legs 2, 3 to the anatomical conditions of a bone.

FIG. 6 shows the osteosynthesis plate 1 as per FIG. 1 for attending to an osteotomy of the olecranon. For reasons of simplicity, the figure only shows the ulna 11 and no further bones of the elbow joint. This embodiment of the osteosynthesis plate according to the invention is particularly suitable for treating simple osteotomies or non-comminuted fractures, in which no more than two fragments have to be fixed. A fracture 20 in the olecranon is treated by using the plate 1. The osteosynthesis plate 1 is preferably first of all adapted to the anatomical conditions by bending. As shown in FIG. 3, the legs 2, 3 are bent such that the epiphyseal ends 25 thereof come to rest against the proximal fragment 13 of the olecranon. The osteosynthesis plate 1 is preferably firstly fixed onto the proximal/epiphyseal fragment by two bone screws 16. A bone screw 15 can thereafter be placed into the long-hole 10 and tightened a little such that the long-hole 10 may still glide. Forceps can now be used to pull the osteosynthesis plate 1 in the distal/diaphyseal direction in order to exert a compression force onto the fracture or osteotomy site. The osteosynthesis plate 1 may then be fixed by tightening the screw 15 in the long-hole 10 and/or by inserting further screws into the openings lying on the distal/diaphyseal fragment whilst maintaining the desired compression force.

FIGS. 7a to 7c show a further embodiment of the osteosynthesis plate 1 according to the invention from different views, the plate being configured such that it may be fitted for treating a comminuted fracture of the olecranon with a plurality of fragments 21, 22, 23, 24. The legs 2, 3 are provided such that they can be placed on the ulna 11 on both sides and the epiphyseal ends can easily be placed on the proximal surface 13 of the olecranon by bending. Since this embodiment of the osteosynthesis plate 1 is provided not only for absorbing tensile forces but should also fix a plurality of bone fragments as stably as possible, it has a thicker design than the plate in FIGS. 1 and 3. So that the legs 2, 3 may nevertheless still be bent to a sufficient extent, they have notches 14 between the openings 5. Both legs 2, 3 have a plurality of openings 5 for fixing the plurality of fragments. The plate 1 is affixed to the ulna 11 by means of bone screws 15, 16.

As illustrated in FIGS. 6 and 7a to 7c, the olecranon remains uncovered on the dorsal side in the epiphyseal section 13 of the osteosynthesis plate 1. Hence the osteosynthesis plate 1 does not bother the patient when placing the forearm on a table, for example, and does not irritate the soft tissue in this region either.

FIG. 8 shows a further embodiment of the osteosynthesis plate 1 according to the invention. Here, the two legs 2, 3 are slightly bent in the plane of the plate. The bridge element 4 extends over a greater area than in the embodiment shown in FIG. 1. The openings 5 are arranged asymmetrically with respect to one another in order to minimize the probability of the anchoring elements clashing together within the bone. The shape of the legs 2, 3 bent in advance is particularly configured to bend the epiphyseal ends 25 of the legs 2, 3 over the external curvature of the bone epiphysis. Here, the region in which the tendons and ligaments radiate into the bone remains largely unaffected by the plate 1. The two openings 18 at the epiphyseal end 25 of the legs 2, 3 allow the introduction of anchoring elements into the bone in the direction from the epiphyseal end 25 to the diaphyseal end 26.

FIG. 9 shows a further variant of the osteosynthesis plate 1 according to the invention. Here, the legs 2, 3 are interconnected by two bridge element 4. One bridge element interconnects the diaphyseal ends 26 of the two legs 2, 3 in an arced fashion, while the second bridge element interconnects the two legs 2, 3 a little further in the direction of the epiphyseal end 25. In this embodiment, too, the region in which tendons and ligaments radiate into the bone remains largely unaffected by the plate. Here, the two bridge elements 4 are configured such that at least 60% of the length L2 of the shorter leg 3 has no connection to the longer leg 2. As a result, the plate can be pushed over the fracture site on the bone from one side. This would not be possible in the case of a plate in which the bridge elements are, for example, connected at both ends or in which the bridge elements are arranged such that the legs are not interconnected over only a short distance on both sides.

FIG. 10 shows a variant of the osteosynthesis plate 1 from FIG. 9. Here, the longer leg 2 has a significantly greater extent than the shorter leg 3. Hence the leg 2 can distribute occurring forces over a larger area. The use of such a plate is particularly expedient where significantly higher pressure forces are expected on one side of the bone. Such a plate can also be utilized if there are further fragments to be fixed in the diaphyseal direction, as is the case, for example, in combined forearm-shaft fractures. The leg 2 can also be designed such that the length thereof can be shortened during surgery, for example using a rongeur, in order to be fitted in an optimum fashion to the anatomical conditions of the bone.

FIG. 11 shows a particularly preferred embodiment of the osteosynthesis plate 1. Here, the two legs 2, 3 are connected by means of an individual bridge element 4. An opening 8 is arranged centrally within the bridge element 4 which may also be used to guide an anchoring element through it. In the process, the bridge element 4 is bent over the external edge of the epiphysis and the legs 2, 3 are applied to the sides of the bone. In this case the openings 5 are likewise arranged in an asymmetric fashion. The advantage of such a plate is that fixing is possible using only the sides of the bone and the epiphysis of the latter. In the process, the regions of the bone where the tendons and ligaments radiate into the bone remain largely unaffected by the plate.

FIG. 12 shows an exemplary application of the osteosynthesis plate 1 from FIG. 11 on the olecranon 9. The bridge element 4 is bent over the outer edge of the epiphysis, in this case the olecranon 9. The two legs 2, 3 are applied to the side of the ulna 11 on both sides. In this embodiment, an anchoring element may be inserted into the bone through the opening 8 in the bridge element 4, for example in order to anchor the osteosynthesis plate 1 on the epiphysis. However, openings 5 can also be arranged such that the plate 1 can be anchored by these openings in the region of the bone epiphysis. Here, the region E where ligaments and tendons radiate into the bone remains completely uncovered by the osteosynthesis plate 1.

FIG. 13 shows an exemplary application of an osteosynthesis plate 1 whose legs 2, 3 are bent about the external curvature of the epiphysis, exemplarily shown as olecranon 9. The bridge element 4 is configured such that it may be bent over the tension side of the bone, in this case the dorsal edge of the ulna 11. The two legs 2, 3 are arranged such that they may be adapted to the lateral anatomical conditions of the bone and the external curvature of the epiphysis. In the process, the region where tendons and ligaments radiate into the bone, and the dorsal edge, which is only covered by a thin layer of skin, remain completely uncovered by the plate, or are only covered in an unsubstantial fashion by the bridge element 4.

The invention claimed is:

1. A method for treatment of a fractured ulna bone or an osteotomy of a bone in the vicinity of an olecranon of the ulna, wherein the method comprises the following steps:
   a. providing an osteosynthesis plate comprising at least two legs, which are spaced apart by a distance of a minimum of 10 mm and interconnected by two bridge elements that cross in a crossing region, wherein the legs each have a certain length and extend in a longitudinal direction from an epiphyseal to a diaphyseal end of the plate and each comprise at least one opening for holding anchoring elements, wherein a size and shape of the legs and the bridge elements are configured such that the bridge elements in their entirety are applied to a curvature of the bone by bending, in a vicinity of the olecranon such that the legs are applied over their entire length laterally on both sides of the ulna without a portion of the at least two legs covering a dorsal edge, wherein the distance between the epiphyseal end of the plate and the crossing region is at least 60% of the length of the legs or at least 60% of the length of a shorter leg such that the plate can be pushed over a fracture from one side, either from an epiphyseal or a diaphyseal side, without pushing the bridge elements over a region in which tendons or ligaments radiate into the bone, wherein the at least two legs and the bridge elements are configured such that a region where at least one of tendons or ligaments radiate into the bone is not covered by the osteosynthesis plate,
   b. fitting the bridge elements in their entirety to a curvature of the bone by bending,
   c. fitting both sides of the legs over their entire length on both sides of the ulna by bending,
   d. attaching the osteosynthesis plate using bone screws.

* * * * *